US007244717B2

(12) United States Patent
Li et al.

(10) Patent No.: US 7,244,717 B2
(45) Date of Patent: Jul. 17, 2007

(54) MUTAGENIC NUCLEOSIDE ANALOGS FOR THE TREATMENT OF VIRAL DISEASE

(75) Inventors: Ling Li, Seattle, WA (US); Alexander Gall, Woodinville, WA (US); Richard Daifuku, Mercer Island, WA (US)

(73) Assignee: Koronis Pharmaceuticals, Incorporated, Redmond, WA (US)

( * ) Notice: Subject to any disclaimer, the term of this patent is extended or adjusted under 35 U.S.C. 154(b) by 481 days.

(21) Appl. No.: 10/226,799

(22) Filed: Aug. 21, 2002

(65) Prior Publication Data

US 2003/0170872 A1 Sep. 11, 2003

Related U.S. Application Data

(60) Provisional application No. 60/314,728, filed on Aug. 24, 2001.

(51) Int. Cl.
*A61K 31/70* (2006.01)
*C07H 19/067* (2006.01)
*C07H 19/09* (2006.01)

(52) U.S. Cl. .................. 514/50; 514/51; 536/28.54; 536/27.4

(58) Field of Classification Search .............. 514/45, 514/48, 50, 51; 536/27.81, 28.54, 27.4
See application file for complete search history.

(56) References Cited

U.S. PATENT DOCUMENTS

| 4,841,039 A | | 6/1989 | Chu et al. | |
|---|---|---|---|---|
| 5,378,693 A | | 1/1995 | McCarthy et al. | |
| 5,849,482 A | * | 12/1998 | Meyer, Jr. et al. | 435/6 |
| 5,935,830 A | * | 8/1999 | Meyer, Jr. et al. | 435/172.1 |
| 6,063,628 A | | 5/2000 | Loeb et al. | |
| 6,136,601 A | * | 10/2000 | Meyer, Jr. et al. | 435/375 |
| 6,521,601 B1 | * | 2/2003 | Carman | 514/44 |

FOREIGN PATENT DOCUMENTS

EP 322384 10/1988

OTHER PUBLICATIONS

Ling et al., "Identification of Alkylidene Hydrazides as Glucagon Receptor Antagonists," *Journal of Medicinal Chemistry*, 44(19), 3141-3149 (Sep. 13, 2001).*
Whale et al., "The Synthesis and Antiviral Activity of (E)-5-(2-nitrovinyl)uridine and (E)-5-(2-nitrovinyl)-2'-deoxyuridine," *Nucleosides & Nucleotides*, 11(2-4), 595-602 (1992); *Chem. Abstracts*, 117, Accession No. 490668, Abstr. No. 90668 (1992).*
Matulic-Adamic et al., "Nucleosides. 150. Synthesis and Some Biological Properties of 5-Monofluoromethyl, 5-Difluoromethyl, and 5-Trifluoromethyl Derivatives of 2'-Deoxyuridine and 2'-Deoxy-2'-fluoro-β-D-arabinofuranosyluracil," *Journal of Medicinal Chemistry*, 31, (8), 1642-1647 (Aug., 1988).*
Huang et al., "5-Substituted 2'-fluoroarabinonucleosides as Potential Antiviral Agents," first disclosed at the "Seventh Symposium on the Chemistry of Nucleic Acid Components," *Nucleic Acids Symposium Series, No. 18*, Bechyne Castle, Czechoslovakia, Aug. 30-Sep. 5, 1987, pp. 261-264.*
Mertes et al., "Synthesis of 5-Formyl-2'-deoxyuridine and the alpha-Anomer," Journal of Heterocyclic Chemistry, 7, 751 (Jun., 1970).*
Aldrich Catalog of Fine Chemicals, Aldrich Chemical Company, Milwaukee, WI, 1994-1995, only p. 720 supplied, see entry 41,417-4 (5-Formyluracil).*
Itahara et al., "Oxidation of Nucleic Acid Related Compounds by the Peroxodisulfate Ion," Bulletin of the Chemical Society of Japan, 67(8), 2257-2264 (Aug., 1994).*
Matulic-Adamic et al., "Nucleosides. 150. Synthesis and Some Biological Properties of 5-Monofluoromethyl, 5-Difluoromethyl, and 5-Trifluoromethyl Derivatives of 2'-Deoxyuridine and 2'-Deoxy-2'-fluoro-β-D-arabinofuranosyluracil," *Journal of Medicinal Chemistry*, 31 (8), 1642-1647 (Aug., 1988).*
Mertes et al., "Synthesis of 5-Formyl-2'-deoxyuridine and the α-Anomer," *Journal of Heterocyclic Chemistry*, 7, 751 (Jun., 1970).*

* cited by examiner

*Primary Examiner*—L. E. Crane
(74) *Attorney, Agent, or Firm*—Townsend and Townsend and Crew LLP

(57) ABSTRACT

The present invention relates to methods of treating viral disease using mutagenic nucleoside analogs. In particular, the invention provides 5-aldehydo-uracil nucleosides and derivatives thereof, and methods of administration thereof to increase the virus mutation rate in a virally infected cell.

6 Claims, 6 Drawing Sheets

|  | Mutations/Nucleotides | % |
|---|---|---|
| Treated MV | 25/15,712 | 0.16 |
| Non-Treated MV | 20/19,605 | 0.10 |

*Fig. 3*

|  | Mutations/Nucleotides | % |
|---|---|---|
| Treated BVDV | 19/12,660 | 0.15 |
| Non-Treated BVDV | 8/19,160 | 0.04 |

*Fig. 5*

MUTAGENIC NUCLEOSIDE ANALOGS FOR THE TREATMENT OF VIRAL DISEASE

CROSS-REFERENCES TO RELATED APPLICATIONS

The present application claims priority to U.S. Ser. No. 60/314,728, filed Aug. 24, 2001, herein incorporated by reference in its entirety.

STATEMENT AS TO RIGHTS TO INVENTIONS MADE UNDER FEDERALLY SPONSORED RESEARCH AND DEVELOPMENT

Not applicable.

BACKGROUND OF THE INVENTION

RNA viral diseases are responsible for the vast majority of viral morbidity and mortality of viral diseases of mankind, including AIDS, hepatitis, rhinovirus infections of the respiratory tract, flu, measles, polio and others. There are a number of other chronic persistent diseases caused by RNA or DNA viruses that replicate through an RNA intermediate which are difficult to treat, such as hepatitis B and C, and T-cell human leukemia. A number of common human diseases are caused by RNA viruses that are replicated by a viral encoded RNA replicase. Included in this group are influenza (Zurcher, et al., *J. Gen. Virol.* 77:1745 (1996), dengue fever (Becker, *Virus-Genes* 9:33 (1994), and rhinovirus infections (Horsnell, et al., *J. Gen. Virol.*, 76:2549 (1995). Important RNA viral diseases of animals include feline leukemia and immunodeficiency, *Visna maedi* of sheep, bovine viral diarrhea, bovine mucosal disease, and bovine leukemia. Although some vaccines are available for DNA viruses, diseases such as hepatitis B are still prevalent. Hepatitis B is caused by a DNA virus that replicates its genome through an RNA intermediate (Summers and Mason, *Cell* 29:4003 (1982). While an effective vaccine exists as a preventive, there is no efficacious treatment for chronic persistent HBV infection.

Currently there is no effective therapy for many viral diseases. While vaccination against influenza can be effective, a new vaccine must be generated each year, depending on the mutations that were fixed in the circulating strain in the previous year, a consequence of the rapid evolution of the viral genome. Current treatment of hepatitis C employs interferon, but it is seldom curative for the disease.

Thus, there exists a need for an effective prevention or amelioration of RNA and DNA virus mediated diseases. The present invention satisfies this need and provides related advantages as well.

SUMMARY OF THE INVENTION

The present invention provides a new strategy for inhibiting viral replication. In the methods of the invention, specified deoxyribonucleoside analogs and ribonucleoside analogs are used to dramatically increase the mutation rate of the virus. This increase in the mutation rate of the virus results in reduced viability of progeny generations of the virus, thereby inhibiting viral replication.

Thus, in one class of embodiments, the invention provides methods of increasing the mutation rate of a virus by administering a DNA or RNA nucleoside analog to a virally infected cell. The cell can be in culture, or present in an animal such as a human patient. The analog is incorporated by an RNA or DNA polymerase into an RNA or DNA copy of a genomic nucleic acid encoding the virus, thereby inducing the virus to mutate.

In preferred embodiments, the nucleoside analog could substitute for one or more of the naturally occurring nucleosides. A template dependent polymerase will incorporate the nucleoside opposite a complementary or non-complementary nucleoside in the template. Subsequent copying of the incorporated analog will result in mutations in the viral genome. This results in variability in template-dependent copies of the nucleic acid. Over time, accumulation of these induced variations (i.e., mutations) causes loss of viability in progeny viruses.

Methods of increasing the mutation rate of a virus in an animal are provided. In the methods, a therapeutically effective dose of an nucleoside analog is administered to the animal. For example, the animal may be a human patient infected with a virus selected from the group consisting of HIV-1, HIV-2, HTLV-1, hepatitis A, hepatitis B, hepatitis C, dengue fever virus. In one embodiment, the nucleoside analog is incorporated by a polymerase present in virally infected cells of the animal into a genomic nucleic acid of the virus with an efficiency range at least about 0.1% that of a naturally occurring complementary nucleic acid. This method provides treatment for, inter alia, AIDS, hepatitis B, hepatitis C and T-cell leukemia. Treatment of non-human infections are also provided, including, but not limited to, feline leukemia virus infections, feline immunodeficiency virus infections, BVDV infections, and vesicular stomatitis virus infections.

Pharmaceutical compositions are provided. The compositions have a therapeutically effective dose of a nucleoside analog and a pharmaceutically acceptable carrier. Preferred nucleoside analogs are those specified herein. Preferred compounds are suitable for oral or parenteral administration.

BRIEF DESCRIPTION OF THE DRAWINGS

FIG. 3 shows mutations induced by treating MV with 5-formyl uridine. Fragment of 1 kb of matrix gene and 1.7 kb of polymerase of cones MV at passage 4, MV treated with 0.15 mM 5-formyl uridine vs. DMSO control.

FIG. 5 shows mutations induced by treating BVDV with 5-formyl-uridine. Fragment of 1 kb glycoprotein gene of clones BVDV at passage 1, BVDV treated with 2 mM 5-formyl-uridine vs. DMSO control.

DETAILED DESCRIPTION OF THE INVENTION

Introduction

Figure 1:
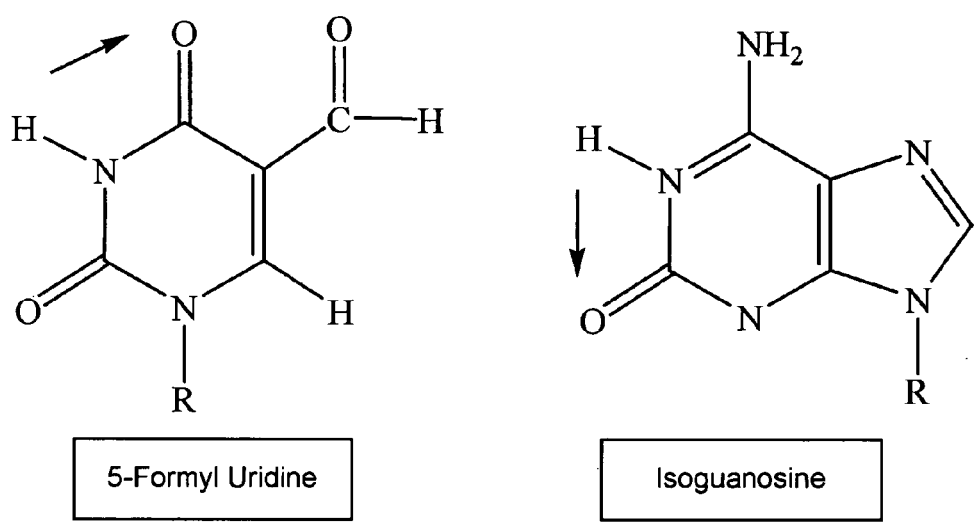
FIG. 1 shows some compounds of the invention.
Figure 2:
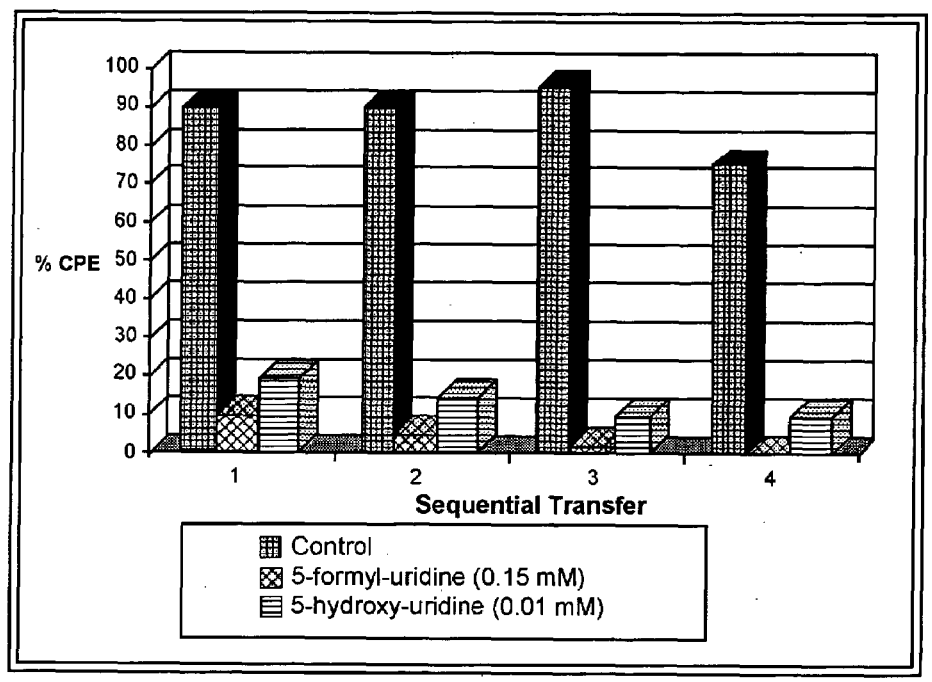
FIG. 2 shows activity against measles virus (MV) of 5-formyl-uridine and 5-hydroxy-uridine compared to DMSO control. Percent CPE refers to the percentage of tissue culture cells demonstrating virally induced cytopathic effect.

In the present invention, 5-formyl-uridine and isoguanosine have been demonstrated to stop replication of viruses such as measles virus and BVDV in vitro after only a few passages. Both of these analogs are able to form tautomers, allowing them to form triple hydrogen bonds. Thus, 5-formyluracyl can pair with guanine instead of adenine, and isoguanine can pair with thymine or uracil instead of adenine. In the case of 5-formyl-uridine, the presence of the aldehyde group at C-5 increases the proportion of the rare tautomer formed by the shift of a proton from N-3 to the oxygen at C-4. It may be capable of other forms of bonding as well. Tautomerism as a basis for causing mutations in viral genomes has previously only been described for deoxy-analogs in an in vitro assay, and to date has never been reported in an intact viral system.

The invention is therefore directed to a method of inducing viral mutagenesis, using 5-formyl-uridine, isoguanosine, and derivatives and variants thereof, which is useful in cell culture as well as in therapy for animals and humans. This method is advantageous in that it is one useful against DNA or RNA viruses (i.e., viruses that have DNA or RNA genomes). In one embodiment, the methods of the invention are advantageous when used to target RNA viruses (viruses with an RNA genome), and retroviruses or other viruses otherwise replicated by an RNA intermediate. In another embodiment, the methods of the invention are advantageous for targeting DNA viruses such as hepatitis B virus, herpesviruses, and papilloma viruses. Without being held to a mechanism of action, in one embodiment, the methods of the invention utilize miscoding nucleosides that are incorporated into both viral encoded and cellular encoded viral genomic nucleic acids, thereby causing miscoding in progeny copies of the genomic virus, e.g., by tautomerism, which allows base mispairing (see, e.g., Moriyama et al., *Nucleic Acids Symposium* 42:131–132 (1999); Robinson et al., *Biochemistry* 37:10897–10905 (1998); Anensen et al., *Mutation Res.* 476:99–107 (2001); Lutz et al., *Bioorganic & Medicinal Chem. Letts.* 8:499–504 (1998); and Klungland et al., *Toxicology Letts.* 119:71–78 (2001)).

The virus may be one in which the viral genomic nucleic acid is integrated into the cellular genome. Examples of viruses which integrate their cellular genome include, but are not limited to, retroviruses. In one particularly preferred embodiment, the virus is HIV. Other preferred viruses include HIV-1, HIV-2, HTLV-1, HTLV-II, and SIV. In another embodiment, the virus is a DNA virus such as hepatitis B virus, herpesviruses (e.g., HSV, CMV, EBV), or papilloma virus (e.g., HPV). Alternatively, the viral genome can be episomal. These include many human and animal pathogens, e.g., flaviviruses such as dengue fever and yellow fever, pestiviruses (a genus of the Flaviviridae family) such as BVDV (bovine viral diarrhea virus), hepatitis C viruses (also a genus of the Flaviviridae family), filoviruses such as ebola virus, influenza viruses, parainfluenza viruses, including respiratory syncytial virus, measles, mumps, the picornaviruses, including the echoviruses, the coxsackieviruses, the polioviruses, the togaviruses, including encephalitis, coronoviruses, rubella, bunyaviruses, reoviruses, including rotaviruses, rhabdoviruses, arenaviruses such as lymphocytic choriomeningitis as well as other RNA viruses of man and animals. Retroviruses that can be targeted include the human T-cell leukemia (HTLV) viruses such as HTLV-1 and HTLV-2, adult T-cell leukemia (ATL), the human immunodeficiency viruses such as HIV-1 and HIV-2 and simian immunodeficiency virus (SIV). In certain embodiments, the virus is hepatitis A or hepatitis B. See, e.g., *Fields Virology* (3$^{rd}$ ed. 1996). Further information regarding viral diseases and their replication can be found in White and Fenner, *Medical Virology* 4th ed. Academic Press (1994) and in *Principles and Practice of Clinical Virology*, ed. Zuckerman, Banatvala and Pattison, John Wiley and Sons (1994).

Preferred compounds for use in the methods of the invention include 5-formyl uridine, isoguanosine, and derivatives and variants thereof. Assays for detecting the mutagenic potential of a nucleoside analog are provided (see, e.g., Example 1). In the assays, the nucleoside analog is incorporated into a viral nucleic acid in the presence of a nucleic acid template, the nucleic acid synthesized by a cellular or viral polymerase, and a determination is made regarding whether the incorporation causes a mutation in a progeny virus. Optionally, naturally occurring (i.e., G, A, U, and/or C) nucleotides are also incorporated into the nucleic acid polymer. The method optionally comprises comparing the rate of incorporation of the nucleoside analog and any naturally occurring ribonucleoside in the assay into the nucleic acid. For additional examples of assays, see, e.g., U.S. Pat. Nos. 6,132,776, 6,130,036, 6,063,628, and 5,512,431, herein incorporated by reference in their entirety.

DEFINITIONS

An amount of compound that increases the rate of viral mutation using assays shown herein or known to those of skill in the art, is a "viral mutation inducing amount" of the compound, which thereby increases or induced viral mutation in a cell or in a subject.

The phrase "increasing viral mutation rate," or "inducing a virus to mutate" in the context of assays for compounds affecting viral mutation, for the purposes of reducing viral infection in a subject, includes the determination of any parameter that is indirectly or directly a measurement of viral mutation. It includes physical, functional and chemical effects, e.g., changes nucleic acid sequence and composition, base pairing, viral titer, cell death, cytopathic effect, viral extinction, and the like.

A "nucleoside" contains a heterocyclic nitrogenous base, either adenine (A), guanine (G), cytosine (C), or uracil (U) joined to a ribose or deoxyribose; upon the addition of a phosphate group the compound becomes a nucleotide. Nucleotides are phosphate esters of nucleosides. The polymerized nucleotides deoxyribonucleic acid (DNA) and ribonucleic acid (RNA) store the genetic information which ultimately controls a cell's or organism's interaction with its environment. Nucleosides or nucleoside analogs of the invention (used interchangeably) are naturally occurring or synthetic.

The four "naturally occurring nucleotides" in RNA and DNA contain adenine, guanine, uracil, thymine or cytosine. Nucleotides which are complementary to one another are those that tend to form complementary hydrogen bonds between them and, specifically, the natural complement to A is U or T, the natural complement to U is A, the natural complement to T is A, the natural complement to C is G and the natural complement to G is C.

A "nucleic acid" is a deoxyribonucleotide or ribonucleotide polymer in either single- or double-stranded form, and unless otherwise limited, encompasses analogs of natural nucleotides.

A "nucleoside analog" as used herein is defined in more detail below and includes analogs of ribonucleosides and deoxyribonucleosides and the triphosphates thereof. As described above, they can naturally occurring or non-naturally occurring, and derived from natural sources or synthesized. These monomeric units are nucleoside analogs (or "nucleotide" analogs if the monomer is considered with reference to phosphorylation). For instance, structural groups are optionally added to the sugar or base of a nucleoside for incorporation into an oligonucleotide, such as a methyl or allyl group at the 2'-0 position on the sugar, or a fluoro group which substitutes for the 2'-O group, or a bromo group on the nucleoside base. The phosphodiester linkage, or "sugar-phosphate backbone" of the oligonucleotide analog is substituted or modified, for instance with methyl phosphonates or O-methyl phosphates.

A "genomic nucleic acid" is a nucleic acid polymer which is homologous to a nucleic acid which encodes a naturally occurring nucleic acid polymer (RNA or DNA) packaged by a viral particle. Typically, the packaged nucleic acid encodes some or all of the components necessary for viral replication. The genomic nucleic acid optionally includes nucleotide analogs. Nucleic acids are homologous when they are derived from a nucleic acid with a common sequence (an "ancestral" nucleic acid) by natural or artificial modification of the ancestral nucleic acid. Retroviral genomic nucleic acids optionally encode an RNA which is competent to be packaged by a retroviral particle. Such nucleic acids can be constructed by recombinantly combining a packaging site with a nucleic acid of choice.

A "virally infected cell" is a cell transduced with a viral nucleic acid. The nucleic acid is optionally incorporated into the cellular genome, or is optionally episomal.

The "mutation rate" of a virus or nucleic acid refers to the number of changes which occur upon copying the nucleic acid, e.g., by a polymerase. Typically, this is measured over time, i.e., the number of alterations which occur during rounds of copying or generations of virus.

An "polymerase" refers to an enzyme (DNA or RNA polymerase) that produces a polynucleotide sequence, complementary to a pre-existing template polynucleotide (DNA or RNA). For example, an RNA polymerase may be either an RNA viral polymerase or replicase or RNA cellular polymerase. A "cellular polymerase" is a polymerase derived from a cell. The cell may be prokaryotic or eukaryotic. The cellular RNA polymerase is typically an RNA polymerase such as Pol II or Pol III. Pol II enzymes are most preferred. A "mammalian RNA polymerase II" is an RNA polymerase II derived from a mammal. A "human RNA polymerase II" is an RNA polymerase II derived from a human. A "murine RNA polymerase II" is an RNA polymerase II derived from a mouse. The polymerase is optionally naturally occurring, or artificially (e.g., recombinantly) produced.

A "cell culture" is a population of cells residing outside of an animal. These cells are optionally primary cells isolated from a cell bank, animal, or blood bank, or secondary cells cultured from one of these sources, or long-lived artificially maintained in vitro cultures which are widely available.

A "progressive loss of viability" refers to a measurable reduction in the replicative or infective ability of a population of viruses over time.

A "viral particle" is a viral particle substantially encoded by an RNA virus or a virus with an RNA intermediate, such as BVDV, HCV, or HIV. The presence of non-viral or cellular components in the particle is a common result of the replication process of a virus, which typically includes budding from a cellular membrane.

An "HIV particle" is a retroviral particle substantially encoded by HIV. The presence of non-HIV viral or cellular components in the particle is a common result of the replication process of HIV which typically includes budding from a cellular membrane. In certain applications, retroviral particles are deliberately "pseudotyped" by co-expressing viral proteins from more than one virus (often HIV and VSV) to expand the host range of the resulting retroviral particle. The presence or absence of non-HIV components in an HIV particle does not change the essential nature of the particle, i.e., the particle is still produced as a primary product of HIV replication.

"Flavivirus" is used to refer to the family Flaviviridae and includes the three genera of the family, the flaviviruses, the pestiviruses (e.g., BVDV), and the hepatitis C viruses (e.g., HCV).

Where the methods discussed below require sequence alignment, such methods of alignment of sequences for comparison are well known in the art. Optimal alignment of sequences for comparison may be conducted by the local homology algorithm of Smith and Waterman (1981) *Adv. Appl. Math.* 2: 482; by the homology alignment algorithm of Needleman and Wunsch (1970) *J. Mol. Biol.* 48: 443; by the search for similarity method of Pearson and Lipman (1988) *Proc. Natl. Acad. Sci. USA* 85: 2444; by computerized implementations of these algorithms (including, but not limited to CLUSTAL in the PC/Gene program by Intelligenetics, Mountain View, Calif., GAP, BESTFIT, FASTA, and TFASTA in the Wisconsin Genetics Software Package, Genetics Computer Group (GCG), 575 Science Dr., Madison, Wis., USA); the CLUSTAL program is well described by Higgins and Sharp (1988) *Gene,* 73: 237–244 and Higgins and Sharp (1989) *CABIOS* 5: 151–153; Corpet, et al., (1988) *Nucleic Acids Research* 16, 10881–90; Huang, et al., (1992) *Computer Applications in the Biosciences* 8, 155–65, and Pearson, et al., (1994) *Methods in Molecular Biology* 24, 307–31. Typically, the alignments are visually inspected and refined manually after computer-aided adjustment.

A preferred example of algorithm that is suitable for determining percent sequence identity and sequence similarity are the BLAST and BLAST 2.0 algorithms, which are described in Altschul et al., *Nuc. Acids Res.* 25:3389–3402 (1977) and Altschul et al., *J. Mol. Biol.* 215:403–410 (1990), respectively. BLAST and BLAST 2.0 are used, with the default parameters described herein, to determine percent sequence identity for the nucleic acids and proteins of the invention. Software for performing BLAST analyses is publicly available through the National Center for Biotechnology Information (http://www.ncbi.nlm.nih.gov/). The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$–$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups which are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$R—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo ($C_1$–$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (up to three rings) which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', —halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, and heteroalkyl, unsubstituted aryl, aryl substituted with 1–3 halogens, unsubstituted alkyl, alkoxy or thioalkoxy groups, or aryl-($C_1$–$C_4$)alkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2$O$CH_3$, and the like).

Similar to the substituents described for the alkyl radical, substituents for the aryl and heteroaryl groups are varied and are selected from, for example: halogen, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —$NRSO_2$R', —CN and —$NO_2$, —R', —$N_3$, —CH(Ph)$_2$, fluoro($C_1$–$C_4$) alkoxy, and fluoro($C_1$–$C_4$)alkyl, in a number ranging from zero to the total number of open valences on the aromatic ring system; and where R', R", R'" and R"" are preferably independently selected from hydrogen, ($C_1$–$C_8$)alkyl and heteroalkyl, unsubstituted aryl and heteroaryl, (unsubstituted aryl)-($C_1$–$C_4$)alkyl, and (unsubstituted aryl)oxy-($C_1$–$C_4$)alkyl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR'$_2$)$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-($CH_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_t$—, where s and t are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted ($C_1$–$C_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1–19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Assays for Mutagenic Nucleosides

In one embodiment, preferred nucleoside analogs of the present invention such as 5-formyl uridine and isoguanosine and derivatives and variants thereof which can be incorporated and extended by a polymerase. Generally, such analogs have phosphodiester linkages allowing them to be extended by the polymerase molecule after their incorporation into RNA or DNA. Thus, unlike certain viral inhibitors which cause chain termination (e.g., analogs lacking a 3'-hydroxyl group), the preferred analogs of the present invention are non-chain-terminating analogs that generally do not result in the termination of RNA or DNA synthesis upon their incorporation. Instead, they are preferably error-inducing analogs, which can be incorporated into an DNA or RNA product but which effectively alter the base-pairing properties at the position of their incorporation, thereby causing the introduction of errors in the RNA or DNA sequence at the site of incorporation.

Determination of parameters concerning the incorporation of altered nucleotides by a polymerase such as, human RNA polymerase II and viral polymerases/replicates or the phosphorylation of nucleoside analogs by cellular kinase, is made by methods analogous to those used for incorporation of deoxynucleoside triphosphates by DNA polymerases (Boosalis, et al., *J. Biol. Chem.* 262:14689–14698 (1987). In selected situations direct determination of the frequency of mutations that are introduced into the viral genome (Ji and Loeb, *Virol.*, 199:323–330 (1994) can be made.

The nucleoside analog is incorporated by a cellular polymerase or viral polymerase into the DNA or RNA copy of the genomic nucleic acid with an efficiency of at least about 0.1%, preferably at least about 5%, and most preferably equal to that of a naturally occurring complementary nucleic acid when compared in equal amounts in an in vitro assay. Thus, an error rate of about 1 in 1000 bases or more would be sufficient to enhance mutagenesis of the virus. The ability of the nucleoside analog to cause incorrect base pairing may be determined by testing and examining the frequency and nature of mutations produced by the incorporation of an analog into DNA or RNA. It has been reported, for example, that the mutation rates in lytic RNA viruses (such as influenza A) are higher than in DNA viruses, at about 300-fold times higher, Drake, *PNAS*, USA 90:4171–4175 (1993). Retroviruses, however, apparently normally mutate at an average rate about an order of magnitude lower than lytic RNA viruses. Id.

For example, in the case of HIV, the viral RNA or the incorporated HIV DNA is copied by reverse transcriptase and then DNA polymerase using a PCR reaction with complementary primers and all four deoxynucleoside triphosphates. The region of the genome copied corresponds to a 600 nucleotide segment in the reverse transcriptase gene. The copied DNA or RNA after 70 rounds of PCR is treated with restriction enzymes that cleave the primer sequences, and ligated into a plasmid. After transfection of *E. coli*, individual clones are obtained and the amplified segment within the plasmid is sequenced. Mutations within this region are determined by computer aided analysis, comparing the individual sequences with control viral sequences obtained by parallel culturing of the same virus in the absence of the RNA analog. For each nucleotide, determinations are carried out after ten sequential rounds of viral passage or at the point of extinction for viral detection. Analogous procedures would be effective for other viruses of interest and would be readily apparent to those of skill in the art.

Incorporation of an analog by a cellular or viral RNA polymerase, by reverse transcriptase (or other viral enzyme) or by DNA polymerase may be compared directly, or separately and the separate test results subsequently compared. A comparison of incorporation of analogs among the polymerases of interest can be carried out using a modification of the "minus" sequencing gel assay for nucleotide incorporation. A 5'-$^{32}$P-labeled primer is extended in a reaction containing three of the four nucleoside triphosphates and an analog in the triphosphate form. The template can be either RNA or DNA, as appropriate. Elongation of the primer past the template nucleotide that is complementary to the nucleotide that is omitted from the reaction will depend and be proportional to the incorporation of the analog. The amount of incorporation of the analog is calculated as a function of the percent of oligonucleotide that is extended on the sequencing gel from one position to the next. Incorporation is determined by autoradiography followed by either densitometry or cutting out each of the bands and counting radioactivity by liquid scintillation spectroscopy.

When a nucleoside analog of the invention is administered to virally infected cells, either in vitro or in vivo, a population of cells is produced comprising a highly variable population of replicated homologous viral nucleic acids. This population of highly variable cells results from administering mutagenic nucleoside analogs to virally infected cells and increasing the mutation rate of the virus population. Thus, the highly variable population of viruses is an indicator that the mutation rate of the virus was increased by the administration of the nucleoside analogs. Measuring the variability of the population provides an assessment of the viability of the viral population. In turn, the viability of the viral population is a prognostic indicator for the health of the cell population. For example, low viability for an HIV population in a human patient corresponds to an improved outlook for the patient.

Preferably, the mutagenic nucleoside analog of choice will be water soluble and have the ability to rapidly enter the target cells. Though generally less desirable, a lipid soluble analog will also have use, particularly where it is necessary to penetrate the blood-brain barrier. The nucleoside analog will be phosphorylated by cellular kinases, if necessary, and incorporated into RNA or DNA.

Preparation of Nucleosides

Compounds of the present invention can be prepared using readily available starting materials or known intermediates. For use in the present inventive methods, the nucleoside derivatives will preferably be prepared as their mono-, di- or triphosphates. The phosphorylation of the nucleoside analogs is typically carried out by enzymatic methods, chemical methods or combinations of enzymatic and chemical methods. Enzymatic phosphorylation can be carried out using a crude source of wheat shoot extract as a source of phosphotransferase activity (see Giziewicz, et al., *Acta. Biocim. Pol.* 22:87–98 (1975); and Shugar, IN MOLECULAR ASPECTS OF CHEMOTHERAPY, Springer-Verlag, 1991, pp. 240–270). Phosphorylation can also be carried out using Herpes virus thymidine kinase or mutants thereof as described by Black, et al., *Biochemistry* 32:11618–11626 (1993). Herpes thymidinekinase has a wide substrate specificity and phosphorylates a wide variety of nucleoside analogs. Purification of the resultant monophosphates can be accomplished using HPLC.

Further conversion of the monophosphate derivatives to the triphosphates will typically use chemical methods such as those provided in Hoard, et al., *J. Am. Chem. Soc.* 87:1785–1788 (1965), incorporated herein by reference.

As is known in the art, nucleosides, nucleosides and analogs thereof can be prepared as racemic mixtures or as enantio-specific compositions which have a prevalence of one or another enantiomeric species (typically greater than about 70% prevalence, more preferably greater than about 90%, still more preferably greater than about 98%). For example, one can obtain or synthesize enantio-specific nucleoside analogs that are predominantly in an unnatural or L-enantiomeric configuration (e.g., by incorporating an L-ribose in place of a D-ribose). Enantio-specific nucleoside compositions can be employed in the context of the present invention to further optimize activity and minimize toxicity. By way of illustration, for a racemic mixture exhibiting activity in the context of the present invention, one of the enantio-specific compositions thereof would typically exhibit greater activity and/or greater specificity (and thus fewer potential side effects at any given concentration) than the other. Enantio-specific compositions of such an analog can therefore be employed to optimize efficacy and/or specificity.

Enantio-specific analogs (and/or other structural variations) can also be employed to influence the intracellular localization of analogs to be used in the context of the present invention. In particular, an enantio-specific or other variant analog can be more efficiently processed by cellular machinery involved in the uptake or intracellular localization of such analogs. For example, one can employ analogs which are preferentially taken up by (and/or localized in the cytosol of) a targeted mammalian cell. Again, by way of illustration, for a racemic mixture exhibiting activity in the context of the present invention, one of the enantio-specific compositions thereof would typically exhibit greater cellular uptake (and/or greater partitioning to the cytosol) than the other. Such structural variations would also be expected to influence the efficiency at which an analog is processed by an enzyme—such as cellular kinases capable of converting a nucleoside to a nucleoside phosphate prior to incorporation, or cellular degradative enzymes such as phosphatases; thereby enabling the isolation of compositions exhibiting greater activity and/or stability.

In addition to the above nucleoside analogs and nucleoside analog triphosphates, the present invention will utilize certain derivatives which are prepared using combinatorial synthesis methods. For example, mixtures of the monomers described above can be protected using standard synthetic methods, then subjected to one or more chemical transformations such as dehydrations, light induced bond scission or isomerization, oxidations, reductions, alkylations, acylations and the like.

Preparation of isoguanosine and analogs thereof

Isoguanosine can be isolated from natural sources (see, e.g., Kim et al., Arch. Pharm Res. 17:115–118 (1994)). Synthesis of isoguanosine and analogs is also known to those of skill in the art. See, e.g., Cottam et al., Nuc. Acids Res. 11:871–882 (1983); Yamazaki et al., Nuc. Acids Res. 3:251–259 (1976); and Marumoto et al., Nuc. Acids Res. 18:37–40 (1987)).

Preparation of 5-formyl uridine and analogs thereof

Oxidation of thymine glycols into 5-hydroxymethyluracils in DNA is a natural process caused by oxidation or γ-irradiation (R. Teoule et al., Radiat. Res., 57, 46 (1974)). Same process has been observed in vitro by treatment of thymine and a number of thymine derivatives with peroxodisulfate ion at 70° (T. Itahara et al., Bull. Chem. Soc. Jpn., 67, 2257–2264 (1994)). The researches have found that other major products, 5-formyluracils are formed along with 5-hydroxymethyluracils in these reactions. We selected this known oxidation of thymine nucleosides and analogs as a general method for synthesis of 5-formyluracil nucleosides and their analogs.

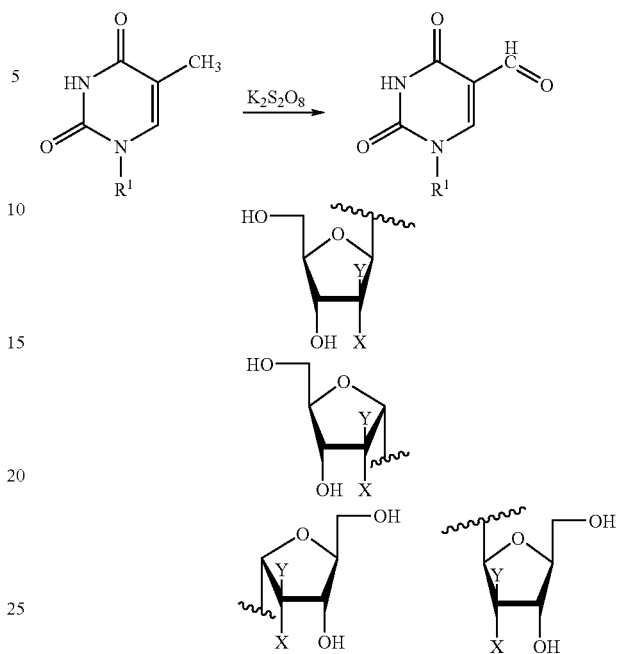

$R^1$=H or sugar residue in
D or L-configuration, in
α or β-anomeric form
where X, Y=H,
or X=OH, Y=H,
or X=H, Y=OH,
or X=F, Y=H,
or X=H, Y=F,
or X=F, Y=F Corresponding glycosylated thymine derivatives are commercially available or can be synthesized by known literature procedures. Thymidine (β-D-sugar form, X=H, Y=H), α-thymidine (α-D-sugar form, X=H, Y=H), 1-β-D-arabinofuranosylthymine (β-D-sugar form, X=H, Y=OH) and 5-methyluridine (β-D-sugar form, X=OH, Y=H) are available from Sigma.

L-Thymidine (β-L-sugar form, X=H, Y=H) can be synthesized by a known method (E. Moyround, et al., Nucleosides Nucleotides 18, 4–5, 1999, 693–696). 5-Methyl-L-uridine (β-L-sugar form, X=OH, Y=H) is also known (E. Moyround, et al., Tetarhedron, 56(11), 2000, 1475–1484). Its α-form (α-L-sugar form, X=OH, Y=H) is reported at (Tougard, Acta Crystallogr. Sect. B., 29, 1973, 2227). Same paper reported 1-β-L-arabinofuranosylthymine (β-L-sugar form, X=H, Y=OH). 1-α-D-arabinofuranosylthymine (α-D-sugar form, X=H, Y=OH) can be synthesized by method (Roberts, Visser J. Am. Chem. Soc., 74, 1952, 668), and its L-isomer 1-α-L-arabinofuranosylthymine (α-L-sugar form, X=H, Y=OH) by (S. Czernecki, et al., Synthesis, 9, 1991, 683–686).

Compounds with fluoromodified sugars are known in a literature. Both 1-(2'-deoxy-2'-fluoro-β-D-arabinofuranosyl)thymine (FMAU) (β-D-sugar form, X=H, Y=F) and 1-(2'-deoxy-2'-fluoro-α-D-arabinofuranosyl)thymine (α-D-sugar form, X=H, Y=F) are known (Tann, C. H., et al., J. Org. Chem., 50(19), 1985, 3644–3647). FMAU can be also synthesized by (K. A. Watanabe, et al., J. Med. Chem. 26(2), 1983, 152–156), and a practical synthesis of its L-isomer (L-FMAU) 2'-deoxy-2'-fluoro-5-methyl-β-L-arabinofuranosyl uracil (β-L-sugar form, X=H, Y=F) is published (J. Du., et al., *Nucleosides Nucleotides* 18, 2, 1999, 187–195). 2'-fluoro-5-methyl-2'-deoxyuridine (β-D-sugar form, X=F, Y=H) can be synthesized by (Codington et al., *J. Org. Chem.*, 29, 1964, 558–563). 2'-Deoxy-2',2'-difluoro-5-methyl-uridine (β-D-sugar form, X=F, Y=F) and its L-isomer 2'-deoxy-2',2'-difluoro-5-methyl-L-uridine (β-L-sugar form, X=F, Y=F) are not known to our best knowledge, but can be synthesized by analogy to known 2'-deoxy-2',2'-difluorouridine (L. W. Hertel et al., *J. Org. Chem.*, 53(11), 1988, 2406–2409).

Most unknown L-nucleoside analogs can be synthesized by following established procedures for known D-nucleosides, since most corresponding starting materials for L-nucleosides are commercially available.

Alternatively, 5-formyluracil nucleosides and analogs can be synthesized by glycosylation of 5-formyluracil with corresponding halosugars. Separable mixtures of α- and β-anomeric forms of nucleoside analogs are normally isolated. This approach can be demonstrated by example of known glycosylation of 5-formyluracil with 2-deoxy-3,5-di-O-p-toluoyl-D-ribofuranosyl chloride (M. P. Mertes, *J. Heterocycl. Chem.*, 7, 1970, 751).

5-Formyluracil nucleosides and analogs can be protected by a number of known methods. Protection of aldehyde groups may be necessary to prevent oxidation of reactive 5-formyluracils to corresponding carboxylic acids in the blood stream or their reaction with proteins. Bioavailability may be also affected by hydrophobicity of the drug molecule which can be tuned-up by an appropriate derivatization/protection of the aldehyde. Release of the active aldehyde may be assisted by change of pH and/or enzymes action inside the cell. Most common acid labile protection of aldehydes is formation of acetals. Optimal stability of acetals can be achieved by selection of an appropriate alcohol for protection of aldehyde group. Typically, cyclic acetals are more stable towards hydrolysis conditions.

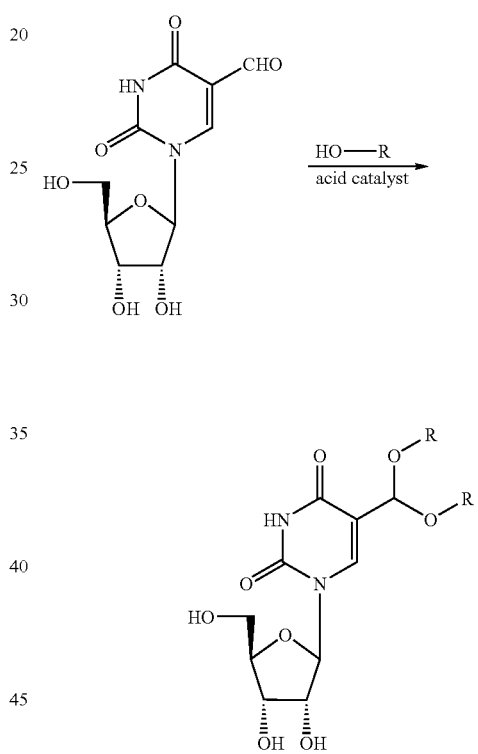

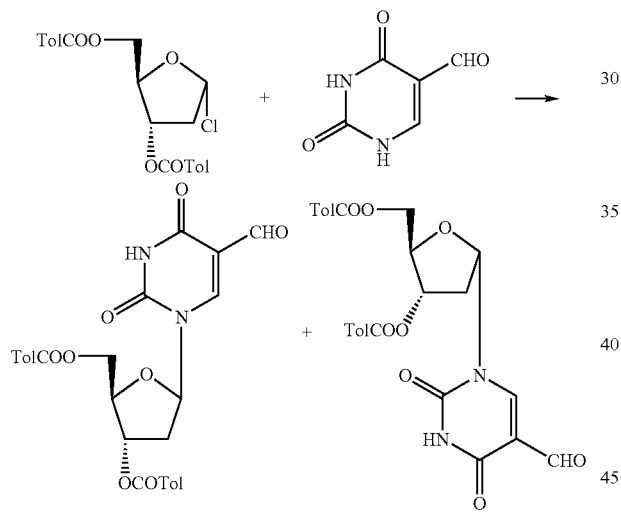

α-Anomeric forms of some nucleoside analogs of 5-formyluracils can be obtained by known base catalyzed anomerization of accessible β-anomers (V. W. Armstrong et al., *Nucl. Acids Res.* 3(7) 1976 pp 1791–1810).

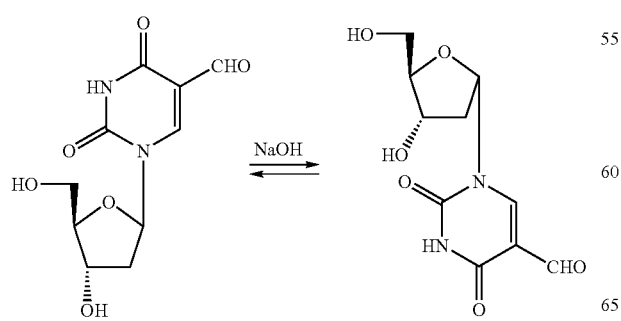

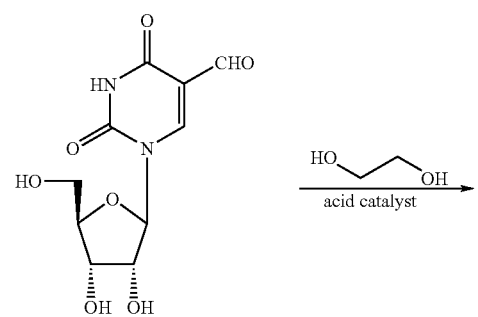

-continued

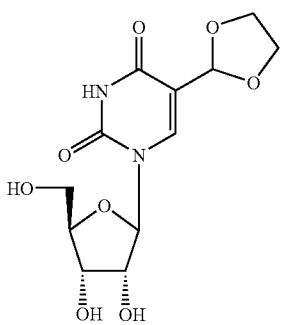

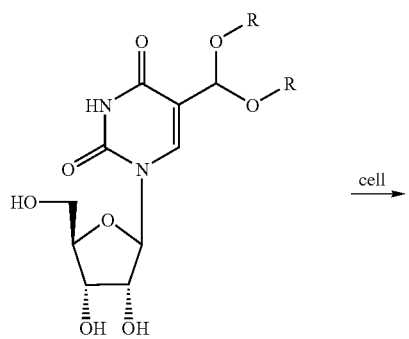

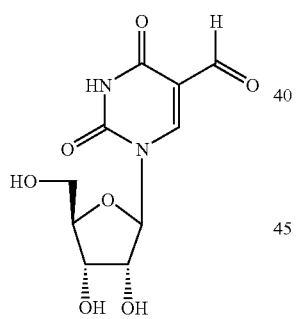

Another common derivatization of aldehydes is formation of hydrazides.

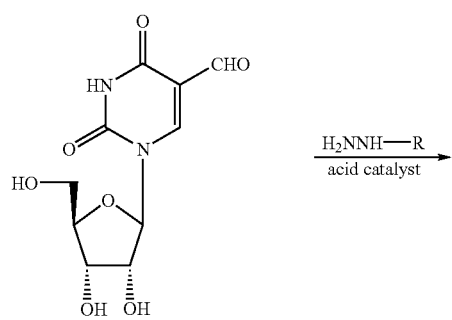

-continued

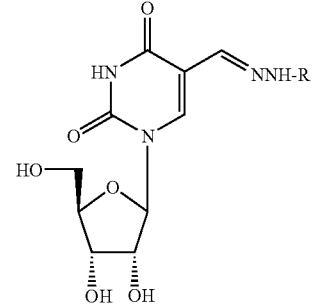

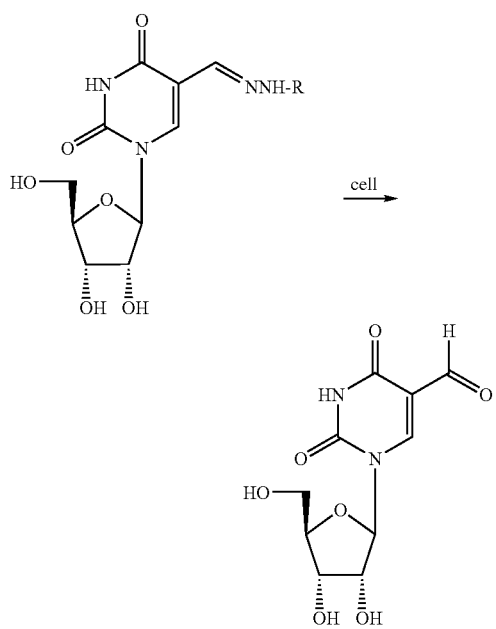

Hydrazides vary by stability depends on pH and a type of the R group. An appropriate derivatization may provide us with a compound which will be releasing an active aldehyde inside the cell under acidic pH of lysosomes or reducing environment.

A number of 5-formyluracils with different sugars can be synthesized. Compound 1-β-D-arabinofuranosyl-5-formyluridine (β-D-sugar form, X=H, Y=OH) has already been synthesized from commercially available 1-β-D-arabinofuranosylthymine (β-D-sugar form, X=H, Y=OH) and now being tested. 5-formyluridines glycosylated with fluoro-modified sugars both in D- and L-forms can also be synthesized. These are novel compounds and we may expect some unusual properties from them. Prodrug forms include aldehydes like acetals and hydrazides.

Administration and Pharmaceutical Compositions

Pharmaceutically acceptable carriers are determined in part by the particular composition being administered, as well as by the particular method used to administer the composition. Accordingly, there are a wide variety of suitable formulations of pharmaceutical compositions of the present invention (see, e.g., *Remington's Pharmaceutical Sciences*, 17th ed., 1989).

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, and intravenous administration are the preferred methods of administration. The formulations of compounds can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

A therapeutically effective amount of a compound is that which results in a measurable decrease of infection or viral titer or which otherwise provides subjective relief of viral symptom(s) or an objectively identifiable improvement as noted by the clinician or other qualified observer.

In therapeutic use for the treatment of viral infection, the compounds utilized in the pharmaceutical method of the invention are administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. The dose administered to a patient, in the context of the present invention should be sufficient to effect a beneficial therapeutic response in the patient over time. The size of the dose also will be determined by the existence, nature, and extent of any adverse side-effects that accompany the administration of a particular compound. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following example is provided by way of illustration only and not by way of limitation. Those of skill in the art will readily recognize a variety of noncritical parameters that could be changed or modified to yield essentially similar results.

Example 1

Activity of 5-formyl-uridine and Isoguanosine in MV or BVDV-infected Cell Culture Cytotoxicity was assayed using graded amounts of nucleoside analog in CV-1 cells or BT cells. 100 pfu of virus was inoculated in $10^5$ CV-1 cells (MV) or BT cells (BVDV). Antiviral activity against MV or BVDV (an HCV surrogate) was tested by passaging the virus in the presence or absence of analog.

Figure 4:
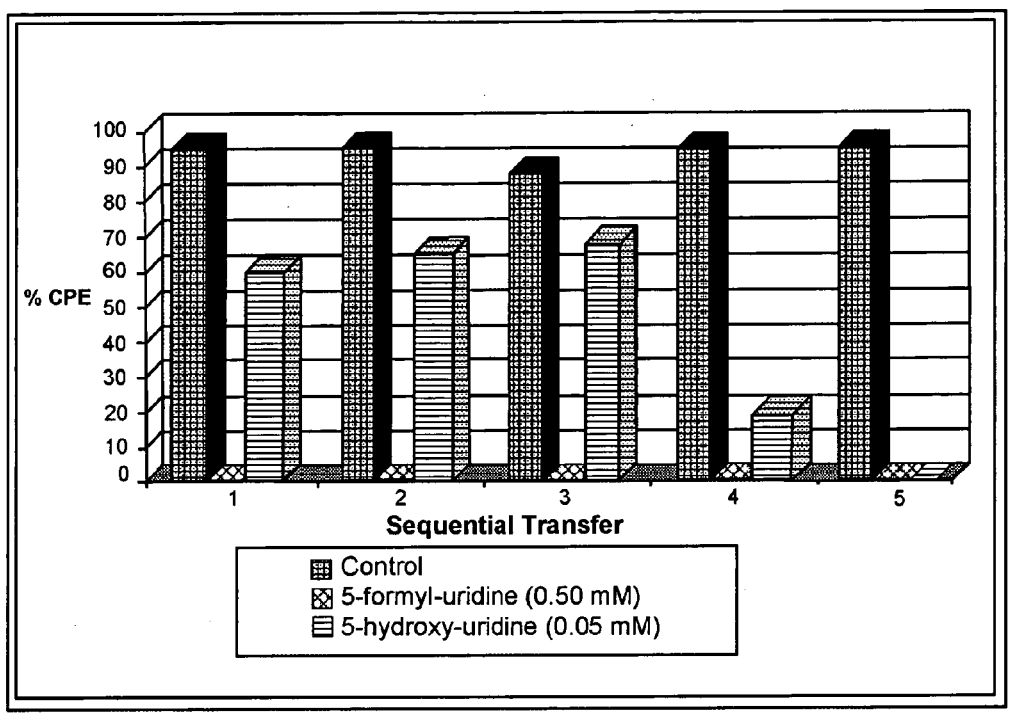
FIG. 4 shows the activity against BVDV for 5-formyl-uridine and 5-hydroxy-uridine compared to DMSO control. Percent CPE refers to the percentage of tissue culture cells demonstrating virally induced cytopathic effect.

In screening experiments, replication of MV or BVDV was assessed by cytopathic effect (CPE) and viral titer after growth in cells for three to four days in the presence or absence of drug. Virus was passaged sequentially until extinction was achieved in the treated group. Experiments were performed in triplicate (see FIGS. 12 and 4).

For 5-formyl-uridine, sequencing was performed to confirm that viral extinction was due to viral mutagenesis by the nucleoside. Clones of MV were selected from treated and control virus at passage 4 and a 1 kb fragment of the matrix and a 1.7 kb fragment of the polymerase were sequenced. As shown in FIG. 3, the mutation rate in the presence of 0.15 mM 5-formyl-uridine is 1.6 fold above the spontaneous mutation rate of MV. A fragment of the BVDV glycoprotein was also sequenced, in which the BVDV virus was treated with 2 mM 5-formyl-uridine. At passage 1, the treated virus had an 3.75-fold increase in mutation in the presence of nucleoside (see FIG. 5).

The $IC_{50}$ of 5-formyl -uridine was greater than 1 mM. At a concentration of 0.5 mM, 5-formyl-uridine completely inhibited MV and BVDV replication within one passage. The $EC_{50}$ was 0.15 mM for both viruses and the $EC_{90}$ was 0.3 mM for MV and 0.4 mM for BVDV.

Figure 6:
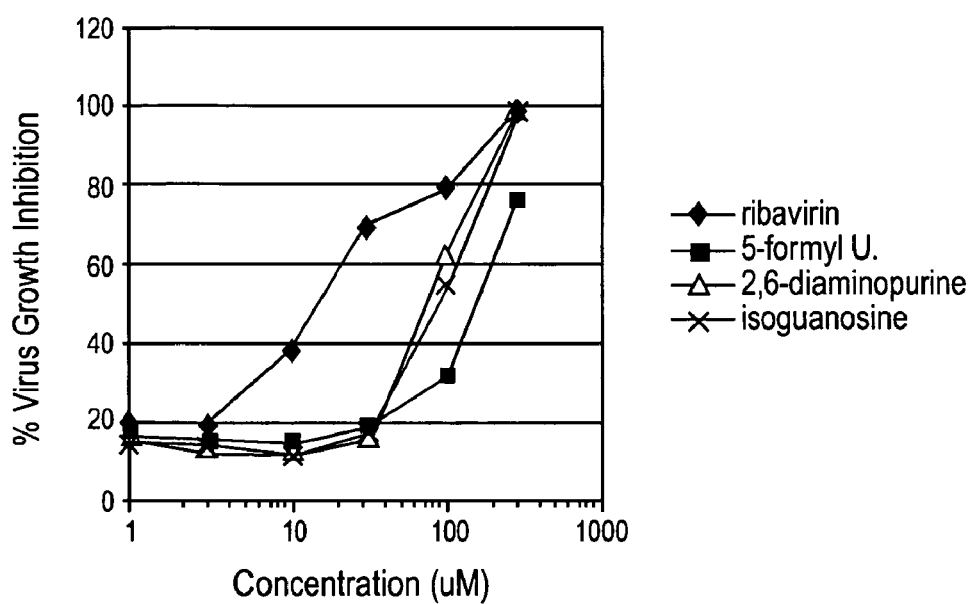
FIG. 6 shows antiviral activity of 5-formyl-uridine, 2,6-diaminopurine riboside, and isoguanosine against BVDV compared to ribavarin.

Isoguanosine and 2,6 diaminopurine riboside were also tested for antiviral activity against BVDV. Viral replication was inhibited after a single passage (see FIG. 6). The EC50 is 70 μM for 2,6 diaminopurine riboside and 80 μM for isoguanosine.

What is claimed is:

1. A method of increasing the mutation rate of an RNA virus, comprising administering a viral mutation inducing amount of a compound to a virally infected cell, wherein the compound has the structure:

wherein, $R^1$ is a member from the group consisting of:

; and

;

$R^6$ and $R^7$ are —H;

Y is selected from the group consisting of —H and —OH,

X is selected from the group consisting of —H and —OH, and at least one but not both of X and Y is —H;

wherein the virus is selected from the group consisting of bovine viral diarrhea virus (BVDV) and measles virus (MV).

2. The method according to claim 1, wherein the cell is in cell culture.

3. The method according to claim 1, wherein the cell is in an animal.

4. The method according to claim 1, wherein the cell is a human cell.

5. The method of claim 1 wherein the RNA virus is measles virus.

6. The method of claim 1 wherein the RNA virus is bovine viral diarrhea virus.

* * * * *